United States Patent
Netsch et al.

(10) Patent No.: US 10,713,220 B2
(45) Date of Patent: Jul. 14, 2020

(54) INTELLIGENT ELECTRONIC DATA CAPTURE FOR MEDICAL PATIENT RECORDS

(71) Applicant: KONINKLIJKE PHILIPS N.V., Eindhoven (NL)

(72) Inventors: Thomas Netsch, Hamburg (DE); Nicole Schadewaldt, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 532 days.

(21) Appl. No.: 15/595,995

(22) Filed: May 16, 2017

(65) Prior Publication Data

US 2017/0337211 A1  Nov. 23, 2017

Related U.S. Application Data

(60) Provisional application No. 62/338,055, filed on May 18, 2016.

(51) Int. Cl.

| | |
|---|---|
| *G06F 17/22* | (2006.01) |
| *G06F 16/16* | (2019.01) |
| *G06F 16/93* | (2019.01) |
| *G06F 16/432* | (2019.01) |
| *G06F 16/178* | (2019.01) |
| *G16H 10/60* | (2018.01) |
| *G06F 19/00* | (2018.01) |
| *G06F 16/34* | (2019.01) |
| *G06F 40/134* | (2020.01) |

(Continued)

(52) U.S. Cl.
CPC ........ *G06F 16/168* (2019.01); *G06F 16/1794* (2019.01); *G06F 16/34* (2019.01); *G06F 16/433* (2019.01); *G06F 16/94* (2019.01); *G06F 19/00* (2013.01); *G06F 40/134* (2020.01); *G06F 40/174* (2020.01); *G16H 10/60* (2018.01); *G06Q 50/24* (2013.01)

(58) Field of Classification Search
CPC ........ G16H 10/60; G16H 15/00; G16H 50/20; G16H 10/20; G06Q 50/24; G06F 3/167; G06F 19/328; G06F 16/951; G06F 16/168; G06F 16/1794; G06F 16/248
See application file for complete search history.

(56) References Cited

U.S. PATENT DOCUMENTS

2015/0365306 A1 * 12/2015 Chaudhri .............. G06F 3/0416 715/736
2016/0259902 A1 * 9/2016 Feldman ............... G06F 19/325

* cited by examiner

*Primary Examiner* — Maroun P Kanaan

(57) ABSTRACT

A device (10) for editing an electronic medical record (EMR) is provided. The device includes a mobile device (12) including a touch-sensitive display (14), a communication link (16), and at least one electronic processor (18) programmed to cause the mobile device to perform an EMR data entry method. The method includes: displaying a medical document (20) on the touch-sensitive display: overlaying an EMR data entry fillable form (22) having user-editable fields (24) on the touch-sensitive display as a partially transparent overlay (26) superimposed on the displayed medical document; transferring text content (28) from the medical document into at least one of the user-editable fields of the overlaid EMR data entry fillable form; and after filling out the overlaid EMR data entry fillable form by operations including at least the transferring, uploading at least the content of the user-editable fields of the filled out EMR data entry fillable form to an EMR (32) via the wireless communication link.

24 Claims, 6 Drawing Sheets

(51) Int. Cl.
*G06F 40/174* (2020.01)
*G06Q 50/24* (2012.01)

FIG. 3

Patient: John Doe   Date of report: XX-XX-20XX
Age: ~           Condition: ~
Height: ~ 28     Weight: ~
                    ((Condition))

Smoking status: non-smoker
                Non-smoker

Report:
Clinical data:

department of pathology

24/06/2011

Freshly received: I: anatom_____ons of lateral-medial 6 cm,
cranial-caudial 5 cm, dorsa  ((Report data))  present therefore not clear
whether it is a properly positioned. Prostate is sprayed. The prostate gland had a weight of 32.5 grams.

27-06-2011

Continued macro. The prostate is linked as pinne              the
right mode is pinned. The prostate is inked as fo   ((Report image))   een
ventral left red. The prostate is laminated in 9 sla             in
PAL GA.

Patient: John Doe  Date of report: XX-XX-20XX
Age: ~  Condition: ~
Height: ~  Weight: ~

((Condition))

Smoking status
Smoker
Non-smoker

Smoking status: non-smoker

Report:
Clinical data:

department of pathology

24/06/2011

Freshly received: l: anatom ons of lateral-medial 6 cm,
craniai-caudial 5 cm, dorsa present therefore not clear
whether it is a properly positioned. Prostate is sprayed. The prostate gland had a weight of 32.5 grams.

27-06-2011

((Report data))

((Report image))

Continued macro. The prostate is linked as pinne    the
right mode is pinned. The prostate is inked as fo    een
ventral left red. The prostate is laminated in 9 sia  in
PAL GA.

INTELLIGENT ELECTRONIC DATA CAPTURE FOR MEDICAL PATIENT RECORDS

FIELD

The following relates to the patient monitoring arts, patient electronic record arts, data transmission arts, and related arts.

BACKGROUND

It is desired to achieve seamless collection of the health information in an electronic health or medical record (EHR or EMR) via flow of digital information through hospital IT infrastructure. The EHR is ultimately intended to provide a "paperless" electronic medical records environment. Unfortunately, in current practice, reports are still printed on paper or image portable document format (PDF) form for the foreseeable future, due for example to legacy systems without sufficient electronic connectivity, receipt of medical reports from outside laboratories lacking electronic connectivity with the hospital, or so forth. Hence, such information has to be transferred back into a corresponding electronic record. For example, paper medical reports from outside laboratories may be scanned and stored in the EMR as a portable document format (PDF) object or some other portable format such as Office Open XML (OOXML or OpenXML) or Open Document Format (ODF). Although relevant pieces of information might be automatically identified in the PDF and matched with the corresponding EHR fields by automated processing algorithms, it cannot be expected that such algorithms will operate with sufficient sensitivity and specificity required in clinical applications.

Presently, such a PDF report is handled as follows. The physician (other another user such as a nurse or technician) reads the PDF report, identifies relevant information (e.g. patient name, demographic data, personal data such as smoker/non-smoker, medical data, or such) and manually re-types or enters the information into appropriate EHR data entry fields. This is a slow and error-prone process. Moreover, physicians are expected to increasingly use mobile devices such as cellphones or tablet computers to perform this task while on-the-go, and the small screen and awkward user interface (touch screen and/or virtual keyboard) make transcription of relevant information from a PDF form into the EHR even more tedious. Conventional copy-and-paste tools may be used, but these are inefficient as the physician must open the PDF window, copy relevant text, and then switch to the EHR data entry window and paste the text into the appropriate GUI dialog. Copy-and-paste user interfacing with mobile devices requires special dexterity, as the user must precisely mark start-and-stop points using the touch-screen.

Further, there is an increasing requirement for structured reporting on patient information, e.g. in cancer registries, disease specific portals or broad studies. These systems have the same issue that information on the patient needs to be converted to a specific electronic form from a variety of sources.

As a result, physicians may still need to read the entire report to identify the required information and/or provide additional cues for semi-automated schemes. While manual form filling by a physician having all reports available (e.g. paper or PDF) is the most reliable form and still standard today, it requires a lot of time, is tedious and inefficient. On the other hand, natural language processing (NLP) algorithms and automated text processing modules do exist, but are not reliable enough to be used regularly in the clinic and require significant manual corrections.

The following provides new and improved devices and methods which overcome the foregoing problems and others.

BRIEF SUMMARY

In accordance with one aspect, a device for editing an electronic medical record (EMR) is provided. The device includes a mobile device including a touch-sensitive display, a communication link, and at least one electronic processor programmed to cause the mobile device to perform an EMR data entry method. The method includes: displaying a medical document on the touch-sensitive display: overlaying an EMR data entry fillable form having user-editable fields on the touch-sensitive display as a partially transparent overlay superimposed on the displayed medical document; transferring text content from the medical document into at least one of the user-editable fields of the overlaid EMR data entry fillable form; and after filling out the overlaid EMR data entry fillable form by operations including at least the transferring, uploading at least the content of the user-editable fields of the filled out EMR data entry fillable form to an EMR via the wireless communication link.

In accordance with another aspect, a device for editing an electronic medical record is provided. The device includes a database configured to store a plurality of electronic medical record fillable forms. A user input device is configured to select a portion of text from at least one medical report. A form editing processor is programmed to: select at least one input field of at least one of the electronic medical record fillable forms; place the selected text from the at least one medical report into the input field of the at least one electronic medical record fillable form; and populate the electronic medical record fillable form when the text from the medical report is moved into the selected input field of the electronic medical record fillable form. A display is configured to display at least one of the at least one electronic medical record fillable form and the at least one medical report.

In accordance with another aspect, a device for editing a document is provided. The device includes a mobile device including a touch-sensitive display, a wireless communication link, and at least one electronic processor programmed to cause the mobile device to perform a data entry method. The method includes: displaying a document on the touch-sensitive display: overlaying a data entry fillable form having user-editable fields on the touch-sensitive display as a partially transparent overlay superimposed on the displayed document; transferring text content from the document into at least one of the user-editable fields of the data entry fillable form; and after filling out the data entry fillable form by operations including at least the transferring, uploading at least the content of the user-editable fields of the filled out data entry fillable form to an electronic record via the wireless communication link.

One advantage resides reduction of paper documents for a user to review.

Another advantage resides in allowing a user to use a mobile device to update medical records.

Another advantage resides in providing indications of text that has been transferred between two documents.

Another advantage resides in providing concurrent and optionally visually linked display of text of a medical document and a data entry fillable form having user-editable fields containing text from the medical document so as to reduce likelihood of error in transferring content from the medical document to the form.

Another advantage resides in providing concurrent display of both a medical document and a related data entry fillable form while maximizing display space occupied by each of the document and the form.

Another advantage resides in providing vocal inputs to edit a medical record.

Further advantages of the present disclosure will be appreciated to those of ordinary skill in the art upon reading and understand the following detailed description. It will be appreciated that any given embodiment may achieve none, one, more, or all of the foregoing advantages and/or may achieve other advantages.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

FIG. 3 shows an example operation of the device of FIG. 1.

FIG. 4 shows another example operation of the device of FIG. 1.

FIG. 5 shows another example operation of the device of FIG. 1.

DETAILED DESCRIPTION

Figure 1:
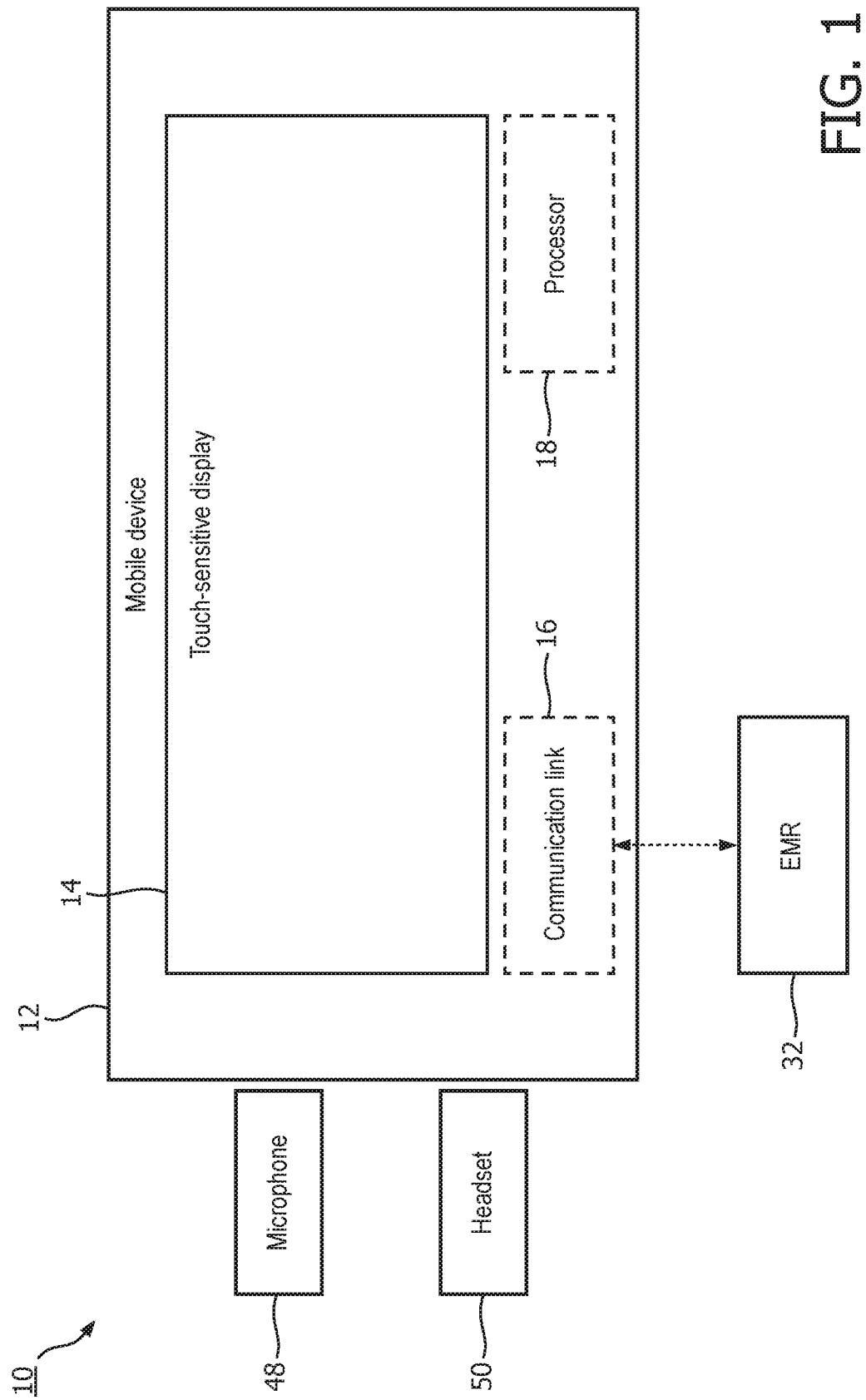
FIG. 1 shows an embodiment of a device to edit an electronic medical record in accordance with one aspect of the present disclosure.
Figure 2:
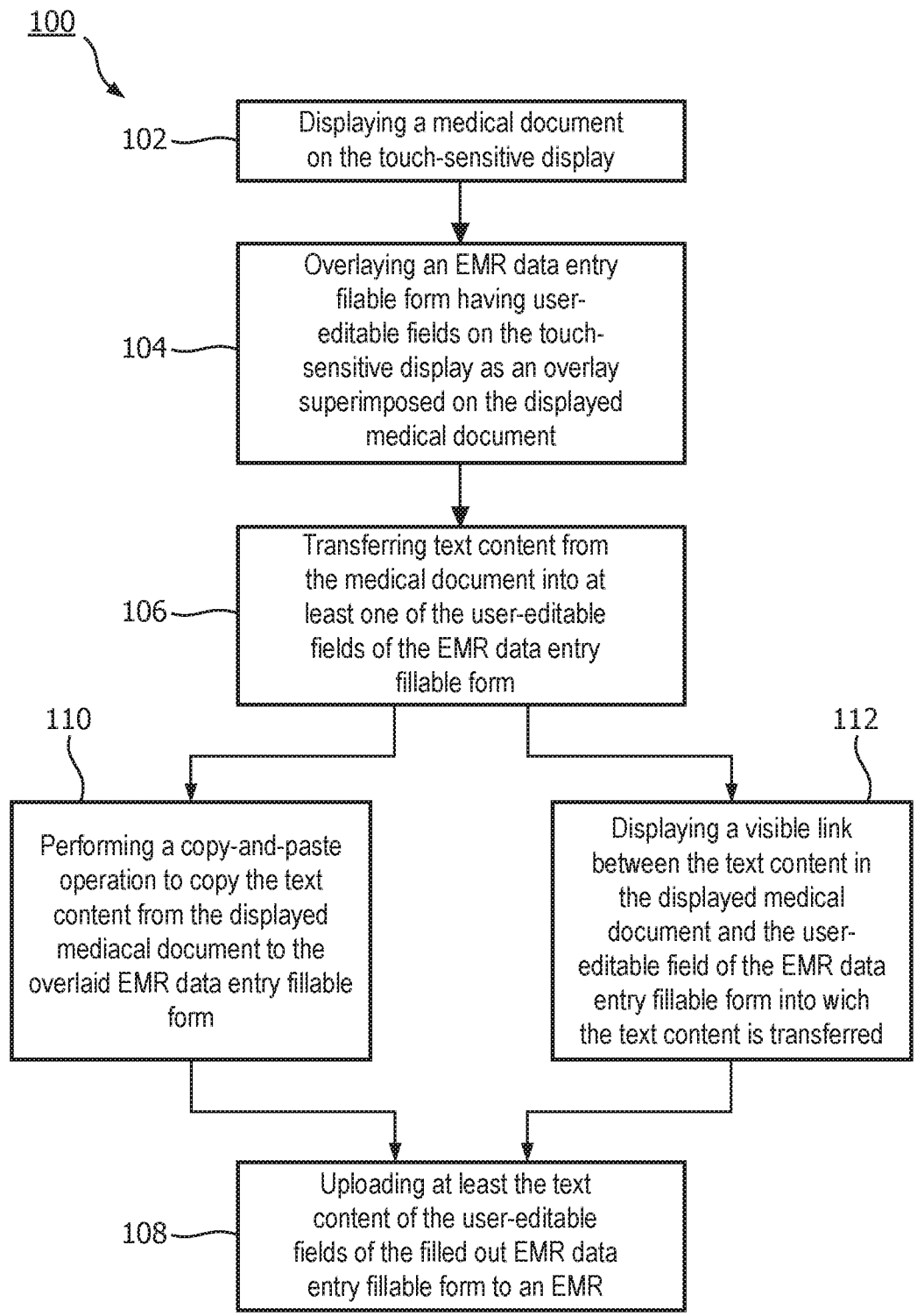
FIG. 2 shows a flowchart showing an exemplary method of use of the device of FIG. 1.

The following discloses several illustrative embodiments for facilitating transcription of selected content of a medical document into a data entry fillable form having user-editable fields. A first embodiment (i.e., an "interactive mode"), displays the EMR form as a partially transparent overlay shown on top of the (for example) PDF document or some other portable format such as Office Open XML (OOXML or OpenXML) or Open Document Format (ODF). This allows the physician to simultaneously see the text of the PDF document that is being copied into the EMR form graphical user interface (GUI) dialog. Copy-and-paste tools can be used with this implementation, with the further variant of enabling "drop and drag" from the PDF to the EMR form GUI dialog. The overlay allows the PDF to occupy the entire screen whereas previously a split-screen would be needed to show both the PDF and the EMR form, or the physician would need to switch between full-screen PDF and EMR form windows.

A difficulty with implementation of the overlay in the context of a touch-sensitive screen is determination of which layer (PDF or EMR overlay) is the target when the user touches a portion of the screen. Some disclosed approaches to disambiguate the target include leveraging force sensitivity of some touch screen displays (e.g. requiring more force to "go through" the overlay and reach the PDF), or contextual disambiguation (for example, a drag-and-drop operation will always start at selected PDF text and end at an EMR form GUI dialog). Transparency-based control is also contemplated, e.g., the touch screen operates on the PDF if the overlay is more than 50% transparent and on the overlay if it is less than 50% transparent.

As yet another possible approach, if the fractional area of the form actually occupied by GUI dialog elements is low, then the touch screen can always operate on the GUI dialog if the touch is within a GUI dialog element zone, and always operate on the PDF otherwise. For this embodiment, it is useful to have separate scroll bars or other mechanism(s) for independently moving the PDF form and/or overlay (or, more generally, for moving one relative to the other), so that if target text of the PDF is obscured by a form GUI dialog the form could be moved relative to the PDF to uncover the target text.

Another disclosed embodiment employs a "computer-aided mode". In this case, the PDF document text is searched for keywords associated with form fields. OCR pre-processing can be employed if the PDF document does not have embedded text. More advanced text content analysis, e.g. natural language processing (NLP) such as part-of-speech parsing, may be used to increase accuracy of the text information extraction. Templates may be used to identify certain pieces of information, for example the patient's social security number (in the United States) should follow the template "###-##-####". The extracted information is then used to populate the form, and the resulting populated form is displayed, preferably again using the partially transparent overlay, with connecting lines indicating where information in the form fields was drawn from the PDF document. In cases in which the information is ambiguous (for example, different parts of the form being contradictory and suggesting both "smoker" and "non-smoker", both options can be included in a drop-down selection list with connecting lines indicating where each option was drawn from the PDF. In this approach, the physician merely reviews/verifies/corrects the populated fields and fills in any additional fields that were not populated by the computer-aided PDF analysis. The overlay and connector lines effectively assist the physician in rapidly performing this review.

It is contemplated to combine the embodiments, e.g. the computer-aided mode may be first run, but the physician is provided with the tools of the interactive mode during the review phase to enable updating a field by drag/drop operations.

A further contemplated aspect is to leverage voice recognition. An advantage of voice recognition in the context of entry of data into a fillable medical form is that the space of allowable vocal segments is vastly reduced for many EMR form fields—for example, a cancer stage field may have only four allowed values: "stage one", "stage two", "stage three", or "stage four". This enables the voice recognition to be much more accurate, making this technology feasible for use in the context of a cellular telephone or tablet computer using a low-fidelity built-in microphone, and possibly with reduced or eliminated speaker-specific training of the voice recognition system. In the computer-aided mode, the space of allowable values may be even more constrained, e.g. the previous example where only two options, "smoker" or "non-smoker", were drawn from the PDF document.

A still further contemplated variant is to replace the two-dimensional PDF/overlay display with a three-dimensional PDF/overlay display using a virtual reality headset, similar to the heads-up display (HUD) technology used by military aviators. In this embodiment, voice recognition and/or eye tracking or gaze tracking could be advantageously used as the user input device.

With reference to FIG. 1, an embodiment of a device 10 for editing an EMR is shown. As shown in FIG. 1, the device 10 includes a mobile device 12. In one example, the mobile device 12 can be a cellular telephone (hereinafter "cell phone"). In another example, the mobile device 12 can be a tablet computer (hereinafter "tablet"). The mobile device 12 includes a touch-sensitive display 14, a communication link 16 (for example, a wireless communication link such as a 3G or 4G cellular link, and/or a WiFi link; or a hard-wired communication link), and at least one electronic processor 18. The processor 18 is programmed through computer readable instructions stored on a medium to cause the mobile device 12 to perform an EMR data method, as described in more detail below. The programming may, for example, be an application program containing computer readable instructions, commonly called an "app", which is loaded onto and executable by the mobile device 12. In such embodiments, the mobile device 12 is typically a general-purpose device that can run any app developed for the mobile device. For example, the mobile device 12 may be an Apple IPhone or iPad running the iOS operating system under which the app executes, or an Android cellphone or tablet running the Android operating system under which the app executes. These are merely illustrative examples and any suitable replacement may be used.

In some embodiments, the mobile device 12 runs one or more computer programs ("apps") that program the mobile device 12 through executable code executing on the electronic processor 18 of the mobile device 12 to perform tasks related to the disclosed EMR data method, with, for example, one or more apps. For example, the app(s) may be computer programs containing lines of software code compiled to form executable code that may be executed on the electronic processor 18. Alternatively, the app(s) may be computer programs containing lines of software code that are read and compiled at run-time by an interpreter (not shown) running on the electronic processor 18 of the mobile device 12, or may be lines of software code compiled into bytecodes or the like which are read and executed at run-time by a virtual machine running on the electronic processor 18 of the mobile device 12.

Referring now to FIGS. 2-6, and with continuing reference to FIG. 1, the one or more processors 18 of the mobile device 12 are programmed, e.g. via an app, to cause the mobile device 12 to perform an EMR data method 100. The method 100 includes: displaying (102) a medical document 20 on the touch-sensitive display 14; overlaying (104) an EMR data entry fillable form 22 having user-editable fields 24 on the touch-sensitive display 14 as a partially transparent overlay 26 superimposed on the displayed medical document 20; transferring (106) text content 28 from the medical document 20 into at least one of the user-editable fields 24 of the EMR data entry fillable form 22 including, for example, at least one of: (1) performing a copy-and-paste operation (110) to copy the text content 28 from the displayed medical document 20 to the overlaid EMR data entry fillable form 22; and (2) displaying (112) a visible link 30 between the text content 28 in the displayed medical document 20 and the user-editable field 24 of the EMR data entry fillable form 22 into which the text content 28 is transferred; and after filling out the EMR data entry fillable form 24 by operations including at least the transferring, uploading (108) at least the text content 28 of the user-editable fields 24 of the filled out EMR data entry fillable form 22 to an electronic medical record (EMR) 32 via the communication link 16. As used herein, an EMR encompasses any type of electronic medical record, whether referred to as an electronic medical record or by some other nomenclature such as an electronic health record, a domain-specific electronic medical record such as a cardiovascular information system (CVIS), or so forth.

At 102, the processors 18 of the mobile device 12 are configured to display a medical document (or record) 20 on the touch-sensitive display 14. For example, the processors 18 are configured to retrieve a selected medical document 20 from a memory (not shown) or database (not shown) associated with the mobile device 12 and display it on the touch-sensitive display 14. The medical document 20 may in general be stored locally on the mobile device 12 or may be wirelessly accessed. The medical document 20 is selected by a user (i.e., a medical professional such as a physician, a nurse, a technician, and the like) of the mobile device 12.

At 104, an EMR data entry fillable form 22 having user-editable fields 24 is overlaid on the touch-sensitive display 14 as a partially transparent overlay 26 superimposed on the displayed medical document 20 (indicated in FIG. 3 as dashed boxes). For example, the EMR data fillable form 22 is also stored in the memory or database associated with the mobile device 12. The form 22 may in general be stored locally on the mobile device 12 or may be wirelessly accessed. The user can also select the EMR data fillable form 22. Once selected, the EMR data fillable form 22 is overlaid onto the medical document 20 on the touch-sensitive display 14 with partial transparency. This allows the user to simultaneously see the text of the medical document 20 that is being copied into the EMR form 22. The overlaid form 22 is displayed as a partially transparent overlay with the transparency controlled by a partial transparency approach such as alpha compositing or blending. Optionally, the degree of transparency (e.g. the alpha value) may be a user-configurable parameter of the app. While in the embodiments disclosed herein the form 22 is displayed as a partially transparent overlay atop the underlying medical document 20, in alternative embodiments the reverse is contemplated, i.e. the medical document may be overlaid with partial transparency atop the form. In this way the display space for each displayed document/form 20, 22 is maximized as compared with, for example, displaying the document and form in smaller separate side-by-side or above-below windows, while enabling both the document 20 and the form 22 to be displayed concurrently, as compared with employing switchable windows.

At 106, text content 28 from the medical document 20 is transferred into at least one of the user-editable fields 24 of the EMR data entry fillable form 22. In one example, at 110, a copy-and-paste operation is performed by the user to copy the text content 28 from the displayed medical document 20 to the overlaid EMR data entry fillable form 22. To do so, the user selects the text content 28 (i.e., by tapping the touch-sensitive display 14, dragging a finger or other object across the touch-sensitive display 14, and the like) to transfer the text content 28 into the user-editable fields 24. In some examples, the copy-and-paste operation 110 includes performing a drag-and-drop operation to drag the text content 28 from the displayed medical document 20 to the overlaid EMR data entry fillable form 22. To do so, when the user selects the text content 28 from the medical document 20, the user drags the text content 28 into the user-editable fields 24 of the EMR data entry fillable form 22. Advantageously, the overlay display approach simultaneously displays both the source text in the medical document 20 and the target location, i.e. the field 24 in the overlaid form 22, so as to facilitate a drag-and-drop operation from the document 20 to the form 22.

However, it will be appreciated that it can be difficult for the medical device 12 to determine whether a user selection using the touch-sensitive display 14 is intended to select a feature in the document 20 or in the form 22, since both are displayed in the same physical screen area. To remedy this problem, the mobile device 12 may be configured to leverage a force sensitivity of the touch-sensitive display 14 (e.g., requiring more force to "go through" the overlay and reach the medical document 20). In one example, the processors 18 of the mobile device 12 are programmed to detect a leveraging force applied by the user to the touch-sensitive display 14 to a selected one of the EMR data entry fillable form 22 and the medical document 20. In other words, the user taps or drags their finger along whichever one of the EMR data entry fillable form 22 and the medical document 20 with which the user wants to interact.

In another example, a drag-and-drop operation can be performed by the user. To do so, the processors 18 are programmed to detect the selected text content 28 from the medical document 20 and detecting an applied force along the touch-sensitive display 14 so that the selected text moves into a selected user-editable field 24 of the EMR data entry fillable form 22. In the drag-and-drop task, the determination of whether the document 20 or the form 22 is being targeted can be addressed by the order of action as follows. In this example, the drag-and-drop operation always starts at selected text 28 of the medical document 20 and end at the user-editable field 24 of the EMR data entry fillable form 22. It will be appreciated that, in this example, during the drag-and-drop operation the medical document 20 always begins with selection of text in the medical document 20, and ends with the drag operation terminating at a field 24 of the form 22. Thus, in a suitable disambiguation approach, the first user selection performed using the touch-sensitive display 14 is associated with the displayed medical document 20, so as to select text of the document. After this first user selection, a second user selection performed using the touch-sensitive display 14 is detected, such as lifting the finger off the screen. This second user selection is associated with the overlaid EMR data entry fillable form 22, and the text selected from the document 20 in the first user selection is dropped into the form field 24 selected in the second user selection.

During the drag-and-drop operation, the processor 18 are programmed to detect text content 28 in the medical document 20 to transfer into the user-editable fields 24 of the EMR data entry fillable form 22 (i.e., from the user selecting the text content). As the user drags the selected text 28 along the touch-sensitive display 14 and into the user-editable fields 24, the processors 18 are programmed to populate the EMR data entry fillable form 22 with the detected text content 28. Thus, the EMR data entry fillable form 22 is updated in real time with the text content 28 of the medical document 20 being dragged into the user-editable fields 24.

In another example, a transparency-based control is also contemplated to transfer the text content 28 into the user-editable fields 24. To do so, the touch-sensitive display 14 is configured operate on the medical document 20 if the overlay 26 (i.e., the EMR data entry fillable form 22) is more than 50% transparent, and on the overlay 26 if it is less than 50% transparent. The processors 18 are programmed to determine the amount of transparency of the overlay 26 by comparing the relative transparencies of each of the medical document 20 and the EMR data entry fillable form 22 relative to each other.

In a further example, if a fractional area of content the overlay 26 (e.g. the fields 24) is low, then the touch-sensitive display 14 may be configured to always operate on the overlay 26 (i.e., the EMR data entry fillable form 22) if the leveraging force applied by the user is within an area of a user-editable field 24 of the EMR data entry fillable form 22, and always operate on the medical document 20 otherwise. For this embodiment, separate scroll bars or other user controls (not shown) can be displayed or employed on the touch-sensitive display 14 for independently moving the medical document 20 and/or the EMR data entry fillable form 22. In this way, if the target text content 28 of the medical document 20 is obscured by the EMR data entry fillable form 22, then the EMR data entry fillable form 22 could be moved relative to the medical document 28 to uncover the target text content 28.

While a drag-and-drop is described, other types of copy-and-paste operations can be similarly implemented. For example, the first user selection can be touching the text to be selected in the medical document 20 (associated to the document 10 as the first operation, or because there is no field 24 at the point of the touch) and the second user operation is then touching the field 24 into which the copied text is pasted. Here there is no drag component.

The foregoing approaches leverage the overlay arrangement of the form 22 overlaid onto the medical document 20 to facilitate copy-and-paste operations, where the simultaneous display of both document 20 and form 22 facilitates the user selection operations in conjunction with approaches just described for disambiguating which is being targeted by the user operation on the touch screen 14. Another benefit of the overlay arrangement is that the copied text in a field 24 can be visually linked to its source in the underlying document 20.

To this end, in another embodiment, at 112, the visible link 30 is displayed between the text content 28 in the displayed medical document 20 and the user-editable field 24 of the EMR data entry fillable form 22 into which the text content 28 is transferred. In one example, the visible link 30 can be displayed as at least one connecting line 34 (e.g., a solid line, a dashed line, an arrow, and the like). Referring to FIG. 3, as an example, the connecting line 34 is shown in FIG. 3 as a thick arrow. The connecting line 34 is arranged or positioned on the display to link the text content 28 selected from the medical document 20 that was inserted into the selected user-editable field 24 of the EMR data entry fillable form 22. The connecting line 34 indicates to the user which text content 28 was transferred into the EMR data entry fillable form 22. The processors 18 are programmed to position the connecting line 34 to connect a position of the text content 28 in the medical document 20 to the user-editable field 24 of the EMR data entry fillable form 22 into which the text content 28 is transferred. For example, if the user wants to enter into a "smoking status" user-editable field 24 of the EMR data entry fillable form 22, the user selects the text context 28 of "smoker" or "non-smoker" from the medical document 20 into the corresponding user-editable field 24. When the text content 28 is transferred, the processors 18 are programmed to display a connecting line 34 from the "non-smoker" text content 28 of from the medical document 20 to the a "smoking status" user-editable field 24. Optionally, the link 34 may be highlighted using a special color, e.g. red.

Figure 4:
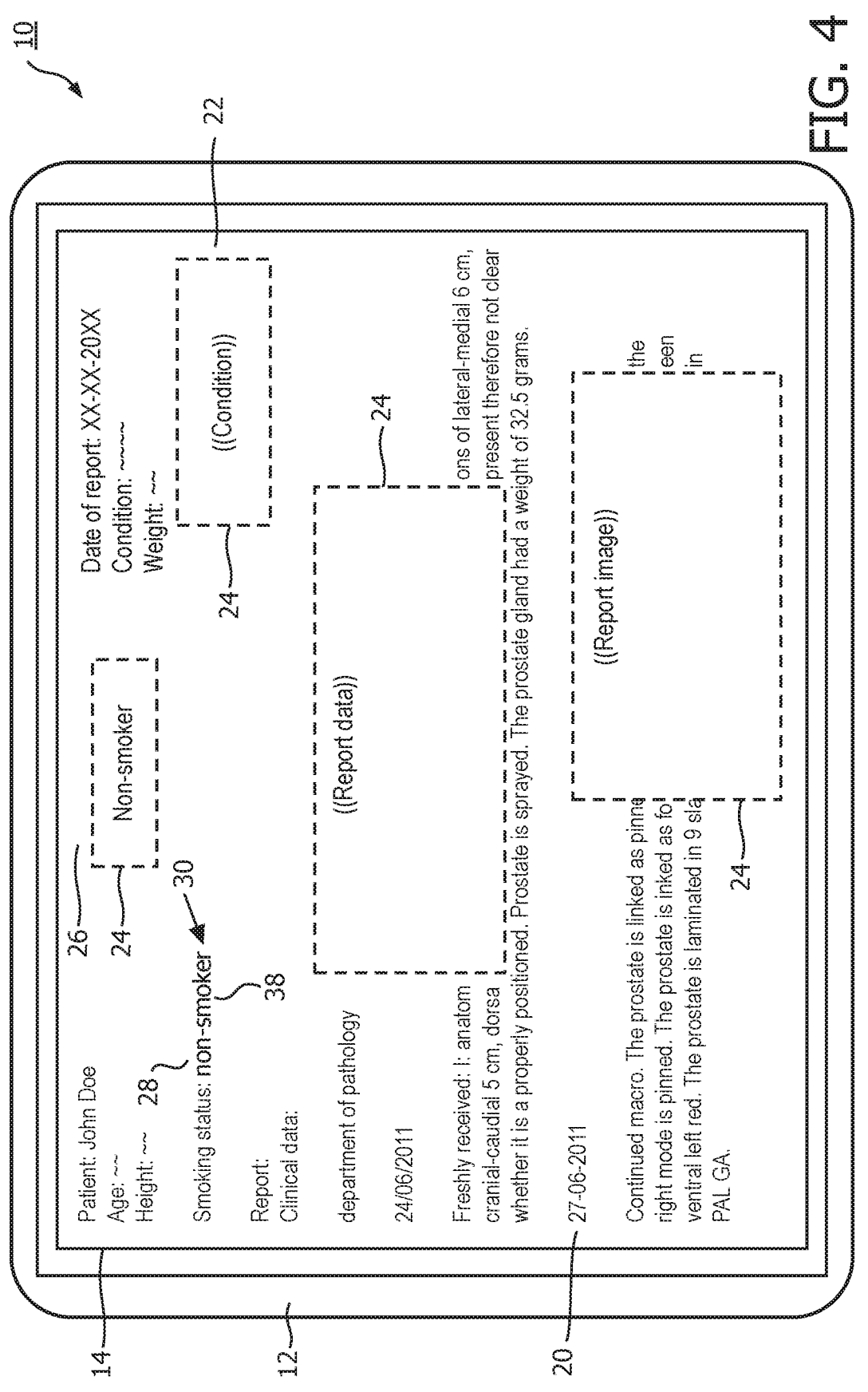

In another example, as shown in FIG. 4, the visible link 30 is configured as highlighted text 38. To do so, the processors 18 are programmed to detect the selected user-editable field 24 into which the text content 28 is transferred by the user. For example, if the user wants to enter into a "smoking status" user-editable field 24 of the EMR data entry fillable form 22, the user selects the text context 28 of "smoker" or "non-smoker" from the medical document 20 into the corresponding user-editable field 24. During the transfer of the text content 28, the processors 18 are programmed to detect that transfer of text from the medical document 20 to the EMR data entry fillable form 22. In the response to this detection, the processors 18 are programmed to highlight the corresponding text content 38 in the displayed medical document 20. To do so, when the text content 28 is transferred, the processors 18 are programmed to highlight the "non-smoker" text content 38 in the medical document 20. As shown in FIG. 4, as an example, the text content 38 is shown as thick black text. It will be appreciated that the color of the highlighted text content 38 can be displayed on the touch-sensitive display 14 in any suitable color (e.g., yellow, orange, blue, red, and the like) to distinguish the highlighted text content 38 from a remainder of the text content 28 of the medical document 20. It will be appreciated that the highlighting 38 and the connecting line 34 can also be used at the same time to emphasize the document source for the field entry.

The highlighting or link is particularly useful in embodiments in which keyword searching, NLP, or another automated process is used to mine the medical document 10 for field entries, since in this case the user is not immediately aware of the source. However, in such automated data entry mining, an extracted field entry may be ambiguous, i.e. two or more different possible values for the field entry may be identified. In a further example, in response to the detection of the selected user-editable field 24 into which the text content 28 is transferred by the user, the processors 18 are programmed to identify two or more text segments from the text context 28 to transfer into a single user-editable field 24. For example, as shown in FIG. 5, in cases in which the information is ambiguous (for example, different parts of the form being contradictory and suggesting both "smoker" and "non-smoker"), the text content 28 of "smoker" and "non-smoker" from the medical document 20 are both displayed in a drop-down selection list 40 including two or more text segments 42 (e.g., a "smoker" text segment and a "non-smoker" text segment). In addition, at least one connecting line 44 (e.g., a solid line, a dashed line, an arrow, and the like) is displayed as being connected to each of the text segments 42 to indicate a location of the text segments 42 in the medical document 20. In this case the user can touch the selection "smoker" or "non-smoker" in the selection list 40 to choose the correct choice, with the connecting line(s) 44 assisting in identifying the textual source for each option in the underlying medical document 20. In another example, the user can select the connecting line 44 of the corresponding desired text segment 42 (e.g., the connecting line connected to the text segment "non-smoker", or the connecting line connected to the text segment "smoker".) On the other hand, if only one entry is extracted for a user-editable filed 24, then it can be displayed in the field, optionally with the connecting line to its source, and the user can merely review, verify, and/or correct the populated single value for user-editable field 24, and can also fill in any additional user-editable fields 24.

In yet another example, in response to the detection of the selected user-editable field 24 into which the text content 28 is transferred by the user, the processors 18 are programmed to search for at least one keyword (not shown) in the selected text content 28 of the medical document 20. The keywords are associated with a selected user-editable field 24 of the EMR data entry fillable form 22. In this example, keyword-searching operations, such as optical character recognition (OCR), natural language processing (NLP), and part-of-speech parsing may be used by the processors 18 to search for the keywords. In another example, one or more templates (not shown) may be used to identify certain pieces of information, for example the patient's social security number should follow the template "###-##-####".

At 108, at least the text content 28 of the user-editable fields 24 of the filled out EMR data entry fillable form 22 is uploaded to the EMR 32 via the communication link 16. To do so, the processors 18 are programmed to upload the completed EMR data entry fillable form 22 (i.e., at least the content of the one or more user-editable fields 24 including text content 28 from the medical document 20) to the EMR 32 for storage therein.

In some embodiments, referring back to FIG. 1, the mobile device 12 further includes a microphone 48 configured to allow the user to dictate the text content 28 from the medical document 20 to the user-editable fields 24 of the EMR data entry fillable form 22. To do so, the mobile device 12 is configured as a voice recognition device to verbally select the selected text context 28 from the medical document 20 into the user-editable fields 24 of the EMR data entry fillable form 22. Advantageously, there may be a limited space of allowable vocal segments for the various user-editable fields 24, and so the possible spoken words or phrases is vastly reduced for many EMR form fields 24. For example, a cancer stage field may have only four allowed values: "stage one", "stage two", "stage three", or "stage four". This enables the voice recognition to be much more accurate, making this technology more practically feasible for use in the context of a cell phone or tablet computer 12 using a low-fidelity built-in microphone 48.

In other embodiments, the mobile device 12 further includes a virtual reality headset 50. The mobile device 12 is configured to display the selected medical document 20 and the selected EMR data entry fillable form 22 as a three-dimensional display (not shown). In this example, voice recognition and/or eye tracking or gaze tracking could be used as a user input device.

Figure 6:
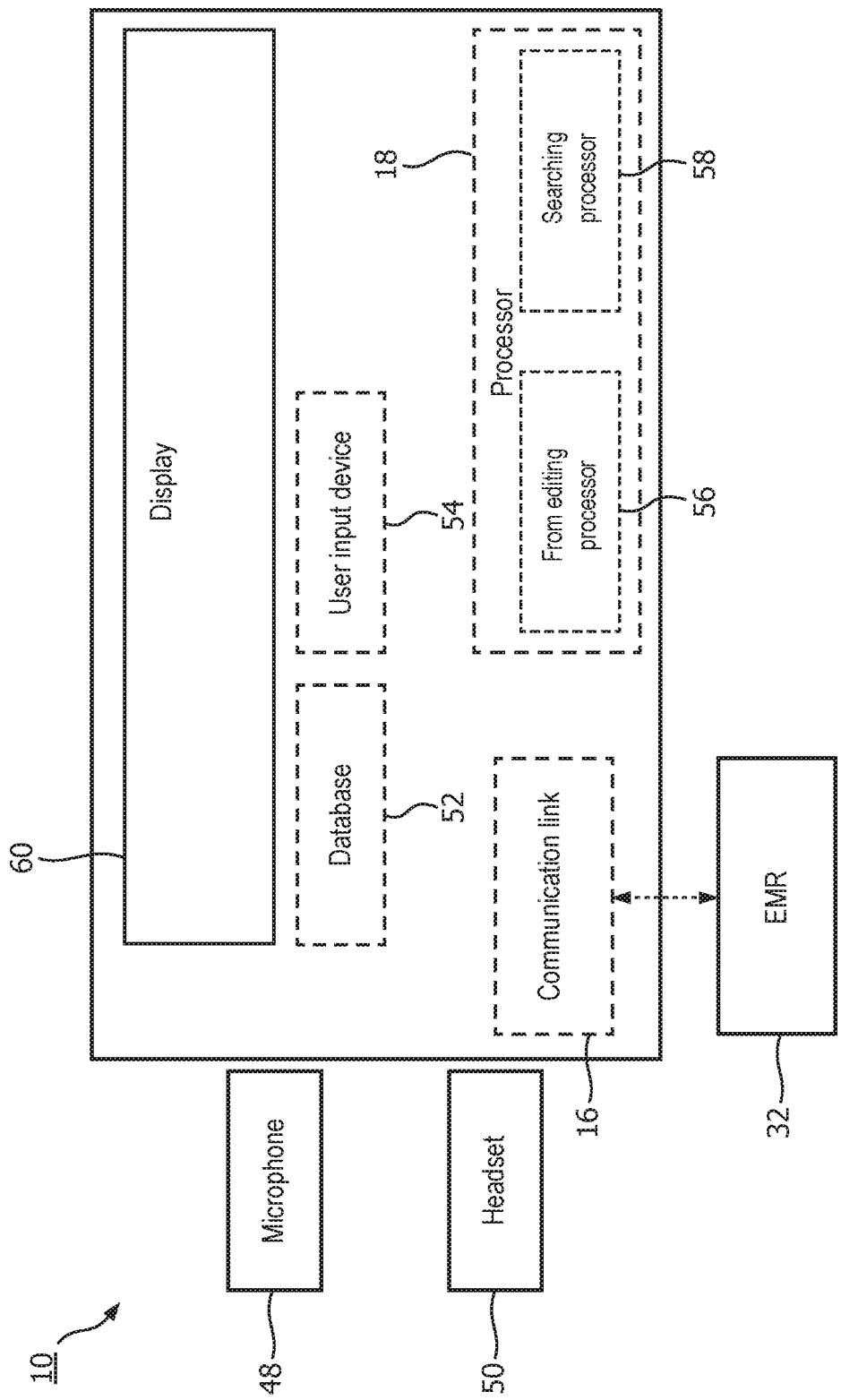
FIG. 6 shows another embodiment of a device to edit an electronic medical record in accordance with one aspect of the present disclosure.

Although the device 10 is described as a mobile device 12, it will be appreciated that the device 10 may also be configured as a desktop computer, a laptop, a workstation, and the like (i.e., a non-mobile device). As shown in FIG. 6, in addition to the components described above (e.g., the communication link 16), the device 10 includes a database 52 configured to store a plurality of the electronic medical record fillable forms 22. The device 10 also includes a user input device 54 configured to select a portion of text 28 from at least one medical report 20. In some case, the user input device 54 can be a mouse, a keyboard, a stylus, and the like. In addition, as described above, the user input device 54 can be the microphone 48, the headset 50, or simply be the user's finger (i.e., on a touch screen). The device 10 can also include the processors 18 described above (and thus programmed to perform the same functions described above). In some examples, the processors 18 can include a form editing processor 56 programmed to: select at least one input field 24 of at least one of the electronic medical record fillable forms 22; and place selected text 28 from the at least one medical report 20 into the input field 24 of the electronic medical record fillable form 22. The processors 18 can also include a searching processor 58 programmed to search for keywords 46 in the selected text 28 of the medical report 20. The keywords are associated with the selected user-fillable field 24 of the EMR fillable form 22.

In addition, the device 10 also include a display 60 configured to display at least one of the electronic medical record fillable forms 22 and at least one of the medical reports 20. The display 60 is configured to populate the electronic medical record fillable form 22 when the text content 28 from the medical report 20 is moved into the selected input field 24 of the electronic medical record fillable form 22. The display 60 is also configured to display a selected electronic medical record fillable form 22 as an overlay 26 over a selected medical report 20. For example, the overlay 26 can be configured as a partially transparent overlay as described above. In another example, the overlay 26 may not be required. For example, one of the medical report 20 and the electronic medical record fillable form 22 can be displayed on a first display (i.e., the touch-sensitive display 14), and the other of the medical report 20 and the electronic medical record fillable form 22 can be displayed on a second display (i.e., the display 60).

It will be appreciated that, while the present disclosure describes editing medical documents, the present disclosure can also be configured for use with any type of editable document.

It will be appreciated that the various documents and graphical-user interface features described herein can be communicated to the various components 12, 14, 32, 48, 50, 52, 54, 60 and data processing components 18, 56, 58 via a communication network (e.g., a wireless network, a local area network, a wide area network, a personal area network, BLUETOOTH®, and the like).

The various components 12, 14, 32, 48, 50, 52, 54, 60 of the device 10 can include at least one microprocessor 18, 56, 58 programmed by firmware or software to perform the disclosed operations. In some embodiments, the microprocessor 18, 56, 58 is integral to the various component 12, 14, 32, 48, 50, 52, 54, 60 so that the data processing is directly performed by the various component 12, 14, 32, 48, 50, 52, 54, 60. In other embodiments the microprocessor 18, 56, 58 is separate from the various component 12, 14, 32, 48, 50, 52, 54, 60. The data processing components 18, 56, 58 of the device 10 may also be implemented as a non-transitory storage medium storing instructions readable and executable by a microprocessor (e.g. as described above) to implement the disclosed operations. The non-transitory storage medium may, for example, comprise a read-only memory (ROM), programmable read-only memory (PROM), flash memory, or other repository of firmware for the various components 12, 14, 32, 48, 50, 52, 54, 60 and data processing components 18, 56, 58. Additionally or alternatively, the non-transitory storage medium may comprise a computer hard drive (suitable for computer-implemented embodiments), an optical disk (e.g. for installation on such a computer), a network server data storage (e.g. RAID array) from which the various component 12, 14, 32, 48, 50, 52, 54, 60 data processing components 18, 56, 58, or a computer can download the device software or firmware via the Internet or another electronic data network, or so forth.

The disclosure has been described with reference to the preferred embodiments. Modifications and alterations may occur to others upon reading and understanding the preceding detailed description. It is intended that the disclosure be construed as including all such modifications and alterations insofar as they come within the scope of the appended claims or the equivalents thereof.

The invention claimed is:

1. A device for editing an electronic medical record (EMR), the device comprising:
   a mobile device including
      a touch-sensitive display,
      a communication link, and
      at least one electronic processor programmed to cause the mobile device to perform an EMR data entry method, wherein the at least one electronic processor is configured to:
         display a medical document on the touch-sensitive display,
         overlay an EMR data entry fillable form having user-editable fields on the touch-sensitive display as a partially transparent overlay superimposed on the displayed medical document,
         display a visible link between text content in the displayed medical document and the user-editable field of the overlaid EMR data entry fillable form into which the text content is to be transferred,
         transfer the text content from the displayed medical document into at least one of the user-editable fields of the overlaid EMR data entry fillable form, and
         after filling out the overlaid EMR data entry fillable form, upload at least content of the user-editable fields of the filled out EMR data entry fillable form to the EMR via the wireless communication link.

2. The device of claim 1, wherein the transferring further comprises:
   performing a copy-and-paste operation to copy the text content from the displayed medical document to the overlaid EMR data entry fillable form.

3. The device of claim 2, wherein performing the copy-and-paste operation further comprises:
   performing a drag-and-drop operation to drag the text content from the displayed medical document to the overlaid EMR data entry fillable form.

4. The device of claim 2, wherein the overlaid EMR data entry fillable form and the medical document are selected by a user by at least one of:
   detecting a leveraging force applied to the touch-sensitive display to a selected one of the overlaid EMR data entry fillable form and the medical document; and
   detecting selected text content from the medical document and detecting an applied force along the display so that the selected text moves into a selected user-editable field of the overlaid EMR data entry fillable form.

5. The device of claim 4, wherein the transferring further comprises:
   detecting text in the medical document to transfer into user-editable fields of the overlaid EMR data entry fillable form; and
   populating the overlaid EMR data entry fillable form with the detected text.

6. The device of claim 2, wherein the copy-and-paste operation further comprises:
   detecting a first user selection performed using the touch-sensitive display and associating the first user selection with the displayed medical documents; and
   after the first user selection, detecting a second user selection performed using the touch-sensitive display and associating the second user selection with the overlaid EMR data entry fillable form.

7. The device of claim 2, wherein the copy-and-paste operation further comprises:
   receiving a user selection via the touch-sensitive display; and:
   associating the user selection with a selected user-editable field of the user-editable fields of the overlaid EMR data entry fillable form after the user selection is at the selected user-editable field, or associating the user selection with the displayed medical document after the user selection is not at any of the user-editable fields of the overlaid EMR data entry fillable form.

8. The device of claim 1, wherein displaying the visible link further comprises:
displaying at least one connecting line linking the text selected from the medical document that was inserted into the selected user-editable field of the overlaid EMR data entry fillable form.

9. The device of claim 8, wherein displaying the visible link further comprises:
detecting selection of the user-editable field of the overlaid EMR data entry fillable form into which the text content is transferred; and
in response to the detecting, highlighting the text content in the displayed medical document.

10. The device of claim 9, further comprising, in response to the detecting:
identifying two or more text segments from the text context to transfer into a single user-editable field; and
displaying a drop-down selection list including the two or more text segments and at least one connecting line to each of the two or more text segments configured to indicate a location of the two or more text segments in the medical document.

11. The device of claim 9, wherein the detecting further comprises:
searching for keywords in the selected text of the medical document, the keywords being associated with the selected user-editable field of the overlaid EMR data entry fillable form.

12. The device of claim 1, wherein the mobile device further comprises:
a microphone and the mobile device is configured as a voice recognition device configured to verbally select the selected text context from the medical document.

13. The device of claim 1, wherein the mobile device further comprises:
a virtual reality headset and the mobile device is configured to display the selected medical document and the selected EMR data entry fillable form as a three-dimensional display.

14. The device of claim 1, wherein the mobile device is either a cellular telephone or a tablet computer.

15. A device for editing an electronic medical record, the device comprising:
a database configured to store a plurality of electronic medical record (EMR) fillable forms;
a user input device configured to select a portion of text from at least one medical report;
a form editing processor configured to:
select at least one input field of at least one EMR fillable; and
place the selected text from the at least one medical report into the input field of the at least one EMR fillable form;
populate the EMR fillable form when the text from the medical report is moved into the selected input field of the at least one EMR fillable form; and
a display configured to display the at least one EMR fillable form and the at least one medical report, wherein a selected EMR fillable form is configured to overlay the at least one EMR fillable form onto a selected medical report, the at least one EMR fillable form being configured as a partially transparent overlay and to display a visible link between text content in the at least one medical report and the at least one EMR fillable form into which the text content is to be transferred.

16. The device of claim 15, wherein the at least one selected EMR fillable form and the selected electronic medical record are selected by a user by at least one of:
detecting a leveraging force applied to the display to a selected one of the EMR fillable form and the medical report; and
detecting selected text content from the medical document and detecting an applied force along the display so that the selected text moves into a selected user-editable field of the EMR fillable form.

17. The device of claim 16, wherein displaying the visible link further comprises:
displaying at least one connecting line linking the text selected from the medical report that was inserted into the selected user-editable field of the EMR fillable form.

18. The device of claim 15, wherein displaying the visible link further comprises:
detecting selection of the user-editable field of the EMR fillable form into which the text content is transferred; and
in response to the detecting, highlighting the text content in the displayed medical document.

19. The device of claim 15, further comprising:
a searching processor programmed to search for keywords in the selected text of the medical report, the keywords being associated with the selected user-fillable field of the EMR fillable form.

20. The device of claim 15, wherein the user input device further comprises at least one of:
a microphone configured to verbally select the selected text from the medical report; and,
a virtual reality headset configured to display the selected medical report and the selected EMR fillable form as a three-dimensional display.

21. The device of claim 15, wherein the at least one EMR fillable form and the at least one medical report are each displayed on the display.

22. The device of claim 15, wherein one of the at least one EMR fillable form and the at least one medical report is displayed on the display, and the other of the at least one EMR fillable form and the at least one medical report is displayed on a second display.

23. A device for editing a document, the device comprising:
a mobile device including a touch-sensitive display, a wireless communication link, and at least one electronic processor programmed to cause the mobile device to perform a data entry method, wherein the at least one electronic processor is configured to:
display a document and a data entry fillable form having user-editable fields on the touch-sensitive display;
overlay one of the displayed data entry fillable form and the displayed document on the touch-sensitive display as a partially transparent overlay superimposed on the other of the displayed data entry fillable form and the displayed document;
display a visible link between text content in the displayed document and the displayed data entry fillable form into which the text content is to be transferred;

transfer the text content from the document into at least one of the user-editable fields of the data entry fillable form; and after filling out the data entry fillable form by operations including at least the transferring, upload at least the content of the user-editable fields of the filled out data entry fillable form to an electronic record via the wireless communication link.

24. The device of claim 23, wherein the transferring further comprises:

performing a copy-and-paste operation to copy the text content from the displayed document to the overlaid data entry fillable form.

* * * * *